(12) United States Patent
Ivinson et al.

(10) Patent No.: US 9,095,964 B2
(45) Date of Patent: *Aug. 4, 2015

(54) DISPOSABLE TORQUE LIMITING DEVICE WITH BELT COUNTER

(71) Applicant: ECA Medical Instruments, Newbury Park, CA (US)

(72) Inventors: David Ivinson, Camarillo, CA (US); John Nino, Simi Valley, CA (US); Gary Norsworthy, Reseda, CA (US)

(73) Assignee: ECA Medical Instruments, Newbury Park, CA (US)

( * ) Notice: Subject to any disclaimer, the term of this patent is extended or adjusted under 35 U.S.C. 154(b) by 227 days.

This patent is subject to a terminal disclaimer.

(21) Appl. No.: 13/772,180

(22) Filed: Feb. 20, 2013

(65) Prior Publication Data

US 2013/0276597 A1 Oct. 24, 2013

Related U.S. Application Data

(60) Provisional application No. 61/635,135, filed on Apr. 18, 2012.

(51) Int. Cl.

| | | |
|---|---|---|
| *B25B 23/157* | (2006.01) | |
| *B25B 13/00* | (2006.01) | |
| *B25B 23/142* | (2006.01) | |
| *B25B 13/46* | (2006.01) | |
| *B25B 15/02* | (2006.01) | |
| *A61B 17/88* | (2006.01) | |
| *B25B 13/48* | (2006.01) | |
| *B25B 13/08* | (2006.01) | |
| *A61B 19/00* | (2006.01) | |
| *A61B 17/00* | (2006.01) | |

(52) U.S. Cl.
CPC .......... *B25B 23/142* (2013.01); *A61B 17/8875* (2013.01); *B25B 13/46* (2013.01); *B25B 13/461* (2013.01); *B25B 15/02* (2013.01); *B25B 23/1427* (2013.01); *A61B 2017/0023* (2013.01); *A61B 2019/301* (2013.01); *A61B 2019/4815* (2013.01); *B25B 13/08* (2013.01); *B25B 13/462* (2013.01); *B25B 13/463* (2013.01); *B25B 13/48* (2013.01); *Y10T 29/4984* (2015.01)

(58) Field of Classification Search
CPC .... B25B 13/462; B25B 13/46; B25B 13/463; B25B 13/48; B25B 13/461; B25B 13/08
USPC ............ 81/58, 58.2, 467, 473–475, 478, 480, 81/57.3
See application file for complete search history.

(56) References Cited

U.S. PATENT DOCUMENTS

2013/0276598 A1* 10/2013 Ivinson et al. .................. 81/467

* cited by examiner

Primary Examiner — Monica Carter
Assistant Examiner — Danny Hong
(74) Attorney, Agent, or Firm — Baker & Hostetler LLP

(57) ABSTRACT

A torque limiting driver with a belt driven use indicator, having a body with a shaft and tool at one end and a counter or indicator at the other end, is disclosed. The indicator is driven by a drive shaft and belt corresponding to movement of the tool. The indicator provides at least one visual cue which corresponds to a predetermined amount of use, or end of life. Alignment of the at least one visual cue with a sight or mark may be used to estimate or determine usage.

17 Claims, 6 Drawing Sheets

DISPOSABLE TORQUE LIMITING DEVICE WITH BELT COUNTER

RELATED APPLICATION

This application claims the full Paris Convention priority benefit of U.S. provisional application No. 61/635,135 filed on Apr. 18, 2012, the contents of which are incorporated by this reference as if fully set forth herein in their entirety.

BACKGROUND

1. Field

This disclosure relates to a medical use driver tool and, in particular, to a torque-limiting driver that disengages at a predefined torque limit and counts a predetermined number of cycles.

2. General Background

Torque-limiting drivers are widely used throughout the medical industry. These torque-limiting drivers have a factory pre-set torque to ensure the accuracy and toughness required to meet a demanding surgical environment.

The medical industry has made use of both reusable and disposable torque-limiting drivers. In a surgical context, there is little room for error and these drivers must impart a precise amount of torque.

Reusable drivers require constant recalibration to ensure that the driver is imparting the precise amount of torque. Recalibration is a cumbersome task but must be done routinely.

Disposable drivers are an easy to use and reliable alternative to the reusable drivers. Typically, each implant, for example, is packaged with a disposable driver designed to the implant's specifications. Once the driver has been used beyond its intended use or intended number of cycles, it can be discarded. Thus, a surgeon can have complete confidence that the disposable driver, packaged with an implant, will impart the precise amount of torque.

Knowing when a disposable driver has reached the predetermined end of its functional life is a desideratum.

DESCRIPTION

Torque is a measure of how much force acting on an object causes that object to rotate. In the case of a driver and a fastener, this measurement can be calculated mathematically in terms of the cross product of specific vectors:

$$\tau = r \times F$$

Where r is the vector representing the distance and direction from an axis of a fastener to a point where the force is applied and F is the force vector acting on the driver.

Torque has dimensions of force times distance and the SI unit of torque is the Newton meter (Nm). The joule, which is the SI unit for energy or work, is also defined as an N m, but this unit is not used for torque. Since energy can be thought of as the result of force times distance, energy is always a scalar whereas torque is force cross-distance and so is a vector-valued quantity. Other non-SI units of torque include pound-force-feet, foot-pounds-force, ounce-force-inches, meter-kilograms-force, inch-ounces or inch pounds.

In some exemplary implementations, aspects of a torque limiting driver with a belt driven use indicator, having a body with a shaft and tool at one end and a counter or indicator at the other end, is disclosed. The indicator is driven by a drive shaft and belt corresponding to movement of the tool. The indicator provides at least one visual cue which corresponds to a predetermined amount of use. Alignment of the at least one visual cue with a sight or mark may be used to estimate or determine usage.

In some exemplary implementation aspects of a torque limiting driver with a belt driven use indicator having a body with a shaft and tool at one end and a counter or indicator at the other end is disclosed wherein a torque limiting driver has a body; a tool engaging tip on a shaft at a first end of said body; a drive shaft rotatable via the movement of said shaft at a second end of said body; an indicator wheel mounted to said body with a top viewable at the second end of the body; and, a belt interposed between said drive shaft and said indicator wheel whereby movement of the drive shaft is translated into rotation of said indicator wheel. In some instance the indicator wheel is within said body and viewed through a sight formed in said body. Moreover, in some instances there is at least one zone with a visual characteristic on said indicator wheel viewable when aligned with said sight. A support post may support the indicator wheel, said support post being formed as part of the body. In some instances a button may be used to affixed, through the top of said indicator wheel, the wheel to the support post. The button may be smaller than the top of the indicator wheel and not block the visual characteristic. The button may, in some instances, cover the top of the wheel and have relocated visual characteristics thereon and viewable via said sight.

In some exemplary implementations, aspects of a torque limiting driver with a belt driven use indicator having a body with a shaft and tool at one end and a counter or indicator at the other end is disclosed. Namely, the implementation consists of a torque limiting driver having a body with a distal end and a proximal end; a tool engaging tip on a shaft at a distal end of said driver; a drive shaft rotatable via the movement of said shaft at said proximal end; an indicator wheel mounted on a support post at the proximal end of the body with a top; a belt interposed between said drive shaft and said indicator wheel, whereby movement of the drive shaft is translated into rotation of said indicator wheel; a mounting means whereby said indicator then is rotatable about said support post; at least one visual indicator on said indicator wheel; and, a sight partially covering the indicator wheel whereby said at least one visual indicator is viewable when it is aligned with said sight. The mounting means may be a button affixed through the top of said indicator wheel to said support post.

In some exemplary implementations, aspects of a torque limiting driver with a belt driven end of life indication is disclosed including placing a rotatable indicator wheel which has visual cue information on it within a body of a disposable torque limiting driver; placing a shaft affixed to a tool inside said body; and, controlling the movement of the indicator wheel with a belt between the shaft and indicator wheel whereby the wheel movement corresponds to the movement of the shaft.

In some exemplary implementations, aspects of a torque limiting driver with a belt driven end of life indication for a disposable torque limiting device, the method including placing a rotatable indicator wheel which has visual cue information on it within a body of a disposable torque limiting driver; placing a shaft affixed to a tool inside said body; and selecting the amount of the movement of the indicator wheel with a belt between the shaft and indicator wheel whereby the wheel movement corresponds to the movement of the shaft.

In some exemplary implementations, aspects of a torque limiting driver with a belt driven end of life indication for a disposable torque limiting device, the method including placing a rotatable indicator wheel which has visual cue information on it within a body of a disposable torque limiting driver;

placing a shaft affixed to a tool inside said body; selecting the amount of the movement of the indicator wheel with a belt between the shaft and indicator wheel whereby the wheel movement corresponds to the movement of the shaft; and, adjusting the diameter of the indicator wheel to vary the amount of movement of the indicator wheel per use cycle of the torque limiting device. The visual cue can be alpha numeric or one of an alpha numeric, color, pattern, mark, or line indicator.

DRAWINGS

The above-mentioned features of the present disclosure will become more apparent with reference to the following description taken in conjunction with the accompanying drawings wherein like reference numerals denote like elements and in which.

Figure 1:
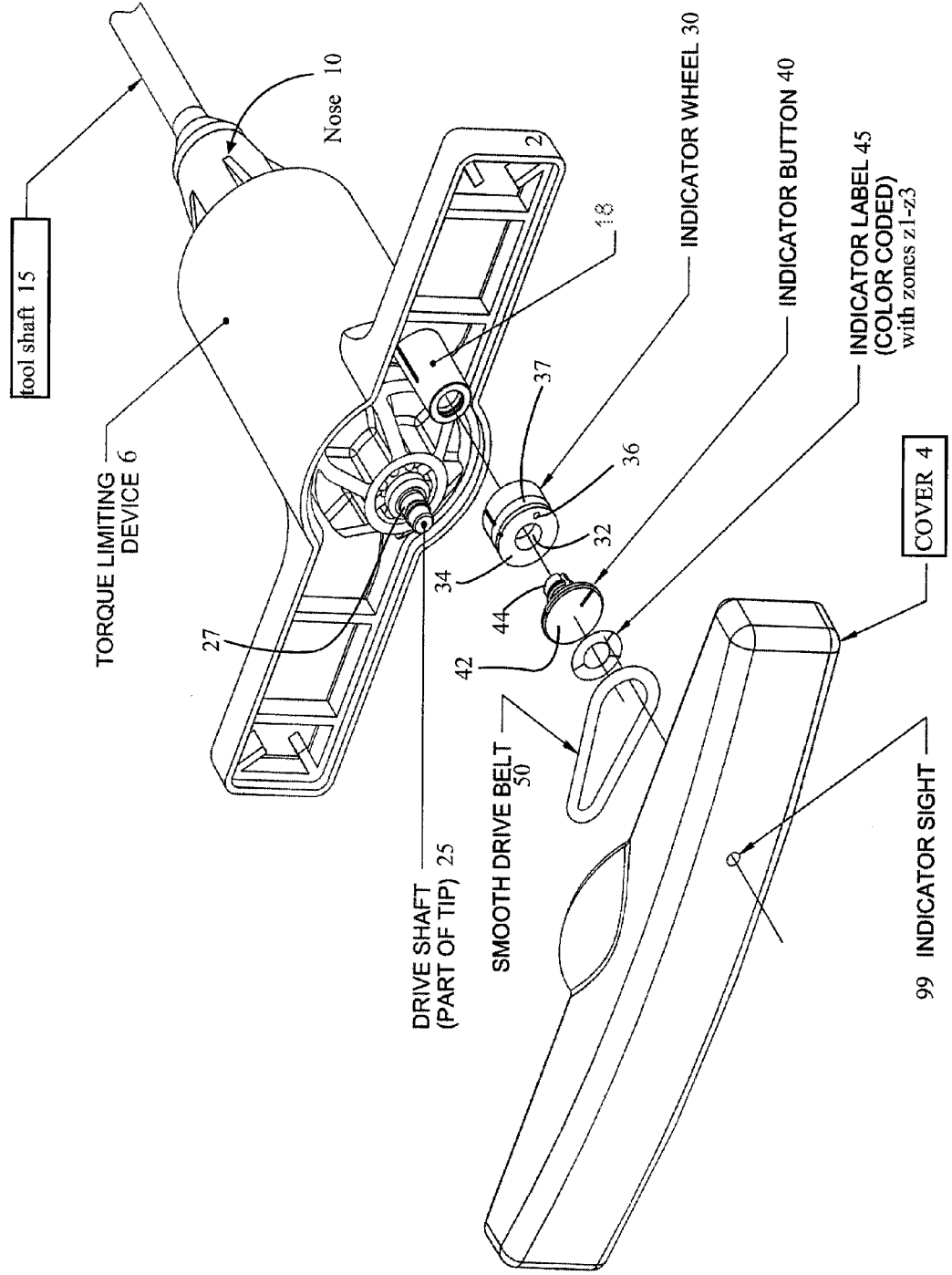
FIG. 1 shows an exploded view of an exemplarily implementation of a torque limiting device belt counter.

While the specification concludes with claims defining the features of the present disclosure that are regarded as novel, it is believed that the present disclosure's teachings will be better understood from a consideration of the following description in conjunction with the appendices, figures, in which like reference numerals are carried forward. All descriptions and callouts in the Figures are hereby incorporated by this reference as if fully set forth herein.

FURTHER DESCRIPTION

Figure 2:
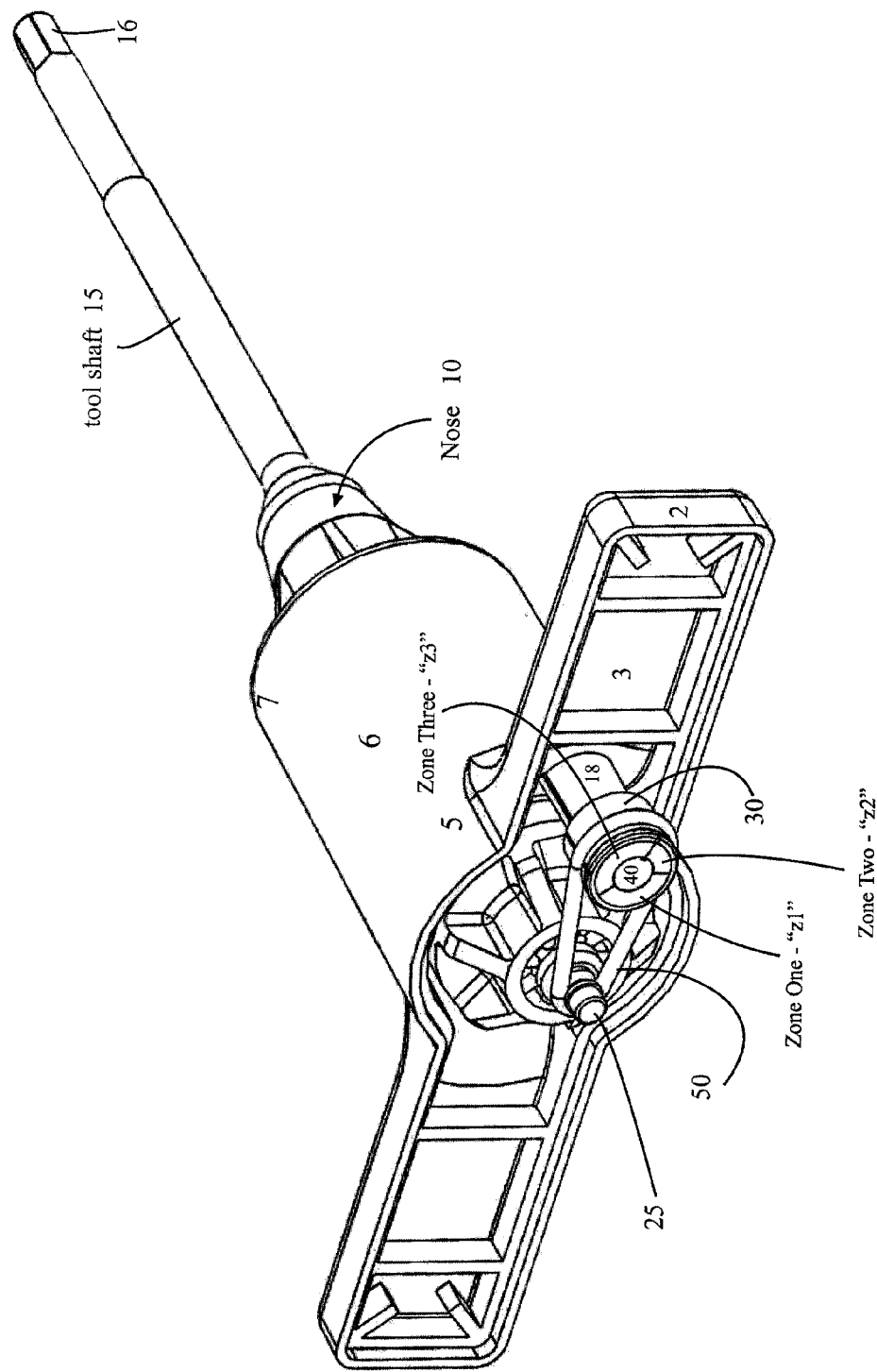
FIG. 2 shows an assembly view of the belt counter portion of a torque limiting device.
Figure 3:
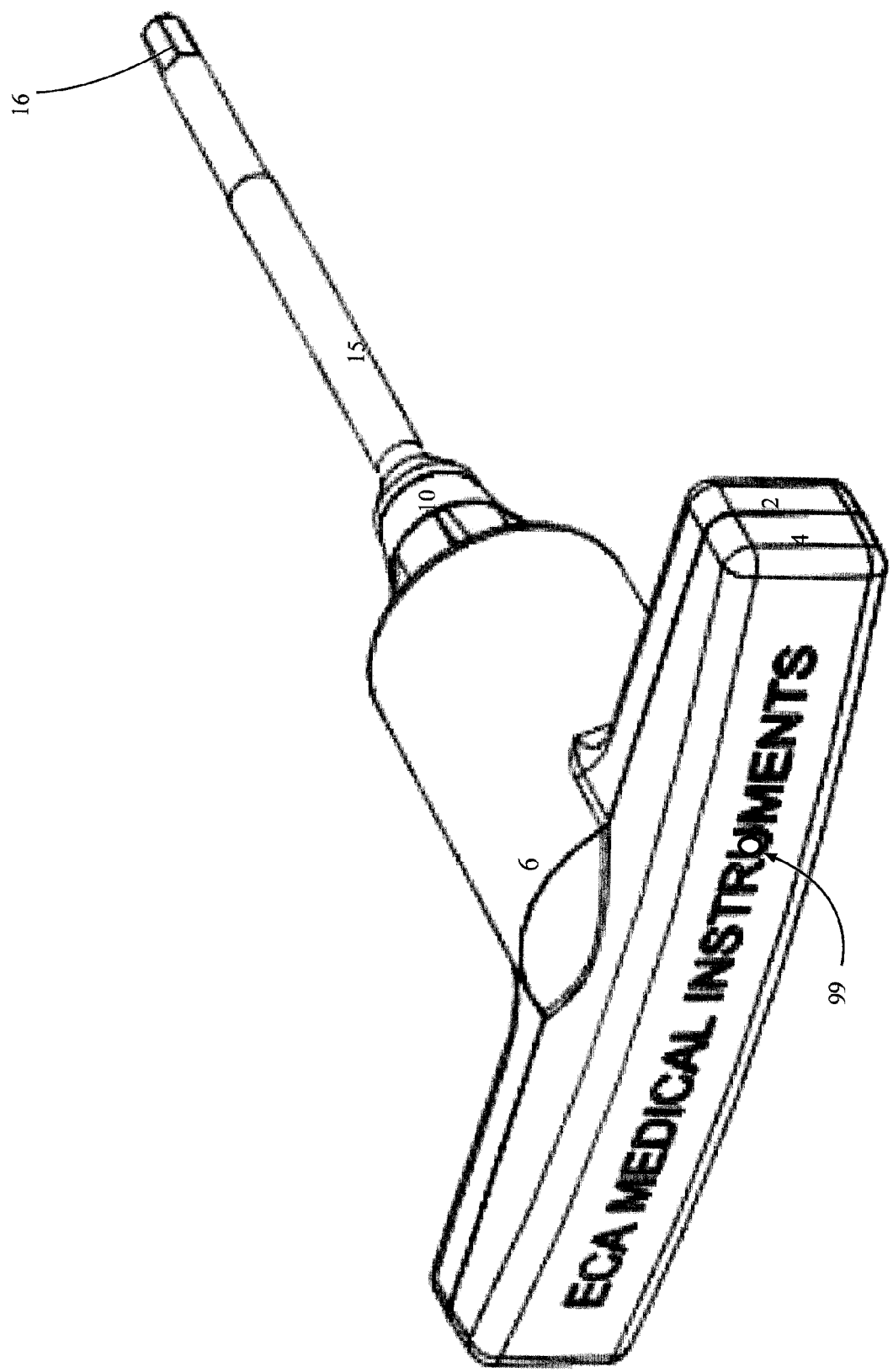
FIG. 3 shows an assembled view of the exemplary implementation in FIG. 2.

Referring to FIGS. 1-3, there is shown a belt counter device affixed to or integrated into the body of a torque limiting driver. A cup 2 having an internal cavity 3 which can be closed via an attachable cover 4 is formed as part of, or attached to, the proximal end 5 of the body of a torque limiting device 6. Cover 4 may be snap-fitted to the cup 2 of the cylindrical body 6, or may be welded, adhered, or attached by any equivalent thereof. Extending from the distal end 7 of the body of the torque limiting device is a nose 10. Extending from the nose 10 and connected to the body of the torque limiting driver 6 is a tool shaft 15 with a tool or tip mount 16 at its remote end.

Placed within the cavity 3 is a belt driven counter mechanism. A support post 18 is formed as part of, or affixed to, the cavity. Apart from the support shaft is a drive shaft 25 (for rotating a belt), which is in line with said tool shaft 15. A belt guide 27 is formed around said drive shaft. An indicator wheel 30 is supported rotatably on said support post 18. The indicator wheel is generally cylindrical with an open bottom central guide 32 fluidly connecting the wheel top 34 with the open bottom, an indicator button guide 26, and a belt wheel guide 37. The indicator button guide is a catch for a latch on the indicator button 40, whereby said indicator button 40 is aligned in a single orientation. The indicator button 40 has a top 42 attached to a leg 44. The leg 44 is of a size and shape to pass through the central guide 32 and mate with the indicator post 18. An indicator label 45 may be affixed to the top 42 of the indicator button. Belt 50 is around the drive shaft 25 and the indicator wheel 30, which provides rotational movement to the indicator button 40 when the torque limiting device imparts torque during use.

Rotation of the indicator wheel 40 spins its top 42. The label 45 affixed to the top will also spin. Said label 45 may have zones (z1-z3 as shown) which are regions of color, texture or graphic to show the movement and current position of the button which corresponds to use of the torque limiting device and/or cycles of use. Said label is optional, and the button top 42 may be pad-stamped or molded to show an equivalent of zones. The zone is a visual cue. During use of the assembled device, an indicator sight 99 provides a partial view of the top of the indicator button 40, wherein zones which change via rotation of said indicator wheel will spin into view via the indicator sight 99. The sight has a partial view of the indicator wheel, whereby a portion of the wheel is hidden under the cover until it is rotated via use of the torque limiting device into alignment with the sight. Visual inspection may then take place at said indicator sight. Inspection may also be via machine vision or other electronic sensor, and is not limited to organic vision. Those of ordinary skill in the art will recognize that it is within the scope of this disclosure that an alpha numeric, color, pattern, mark or line indicator may be used, in lieu of, or in conjunction with, a sight.

Figure 4:
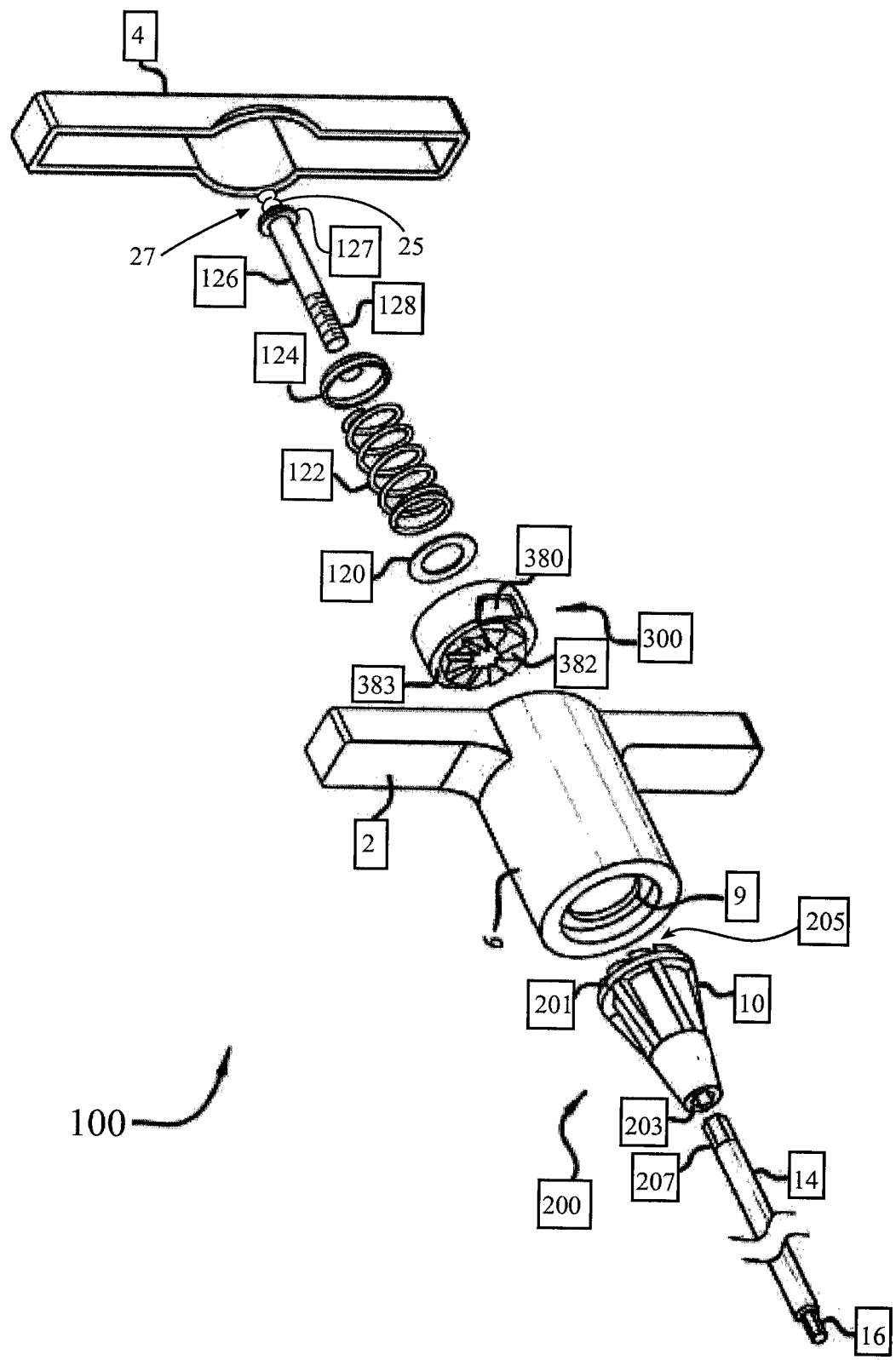
FIG. 4 shows an assembly view of an exemplary implementation of a torque limiting device with belt counter.

Referring to FIG. 4, there is shown an exploded view of a torque-limiting driver 100. The T-shaped handle, which also comprises a part of the "body" of the torque limiting device, forms a cavity 3 with a lower cup 2 and upper cover 4. The cup 2 extends into the generally hollow cylindrical body 6 with a cylindrical distal end 7, opposite the T-shaped handle on the cylindrical body 6 and a circumferential rim 9. At the distal end 7, there is nose 10. The nose contains a lower shank 200 and has a circular annular flange 201 to engage said circumferential rim 9, and annularly tapering body along its length. At one end, the nose 10 tapers to an axial bore 203 at the end of the nose cone 10, molded to engage a shaft 15. The shaft 15 may be hexagonal or cylindrical in transverse cross-sectional shape and is provided, at one end, with a work-piece-engaging tip 16, adapted for engagement with an associated work-piece, such as a fastener or the like. At an opposite end, the lower shank 200 has a plurality of teeth 205 arranged in a crown gear formation. Inside the cylindrical body 6 a clutch assembly is disposed. The clutch assembly includes an upper shank 300 for forcibly engaging the lower shank 200. The upper shank 300 also includes at least one recess 380 on the side of the outer shank. The upper shank 300 has a bottom face that has teeth 382 arranged in a crown gear formation and an annular flange or circumferential rim 383 extending radially outwardly. The recess 380 is provided as a cylindrical cut, relief or recess into the side of the outer shank and may be provided as a square or rectangular cut or the cut may have a slanted side or sides relative to the axis of the upper shank 300.

In assembly, the shaft 15 is received into the axial bore 203 of the lower shank 200. A washer (not shown) in FIG. 4 may be provided between the circumferential rim 9 of the lower shank 200 and the circular annular flange 201.

The opposite side of the circular annular flange 201 receives the circumferential rim 383 of the upper shank 300 allowing the teeth 205 of the lower shank 200 to engage the teeth 382 of the upper shank 300 when a torque is applied. Integrally formed within the cylindrical body 6, is a protrusion that mates with the recess 380 of the upper shank 300. The protrusion 385 extends inward in a radial fashion and has a length along the axis of the cylindrical body 6 for relative moveable engagement within the recess 380. This engagement provides a locking mechanism of the shaft 15 relative to the T-shaped handle via the upper shank when pressure is applied across the lower shank 200 and the upper shank. The recess 380 is provided circumferentially wider than the protrusion 385 for allowing the cylindrical body 6 and the T-shaped handle to rotate in reverse a predetermined distance from a locked position without subsequent reverse rotation of the work-piece-engaging tip 16. Thus, the at least one recess 380 and at least one protrusion 385 lock the T-shaped in one direction, providing the necessary torque to drive a fastener and allow for a predetermined amount of reverse rotation before unscrewing a fastener.

In use, force is applied across the lower shank 200 and the upper shank 300 via a spring 122 within the cylindrical body 6. Inside the cylindrical body 6, a washer 120 is provided between the upper shank 300 and the spring 122. The washer transfers pressure from the spring 122 over the top face of the upper shank 300. At an end of the spring 122 opposite the upper shank 300, a cup washer 124 and a locking screw 126 hold the spring 122 in a compressed state. The locking screw 126 has a threading 128 that engages a complementary threading within an axial bore (not shown) of the lower shank 200. Thus, imparting pressure between the respective teeth 382 of the lower shank 200 and the upper shank 300. The spring 122 and the locking screw 126 provide the proper tensioning and biasing for the clutch assembly and, generally, the locking screw 126 is adjustable to provide proper tension and calibration. Extending axially from the top 127 of said locking screw is drive shaft 25. Applicant's U.S. Pat. No. 7,938,046 teaches a torque limiting device without a belt counter and is hereby incorporated by this reference as if fully set forth herein. Those of ordinary skill in the art will recognize that the locking scree may be replaced by a locking shaft or other fastener, all of which are within the scope of this disclosure.

Figure 5:
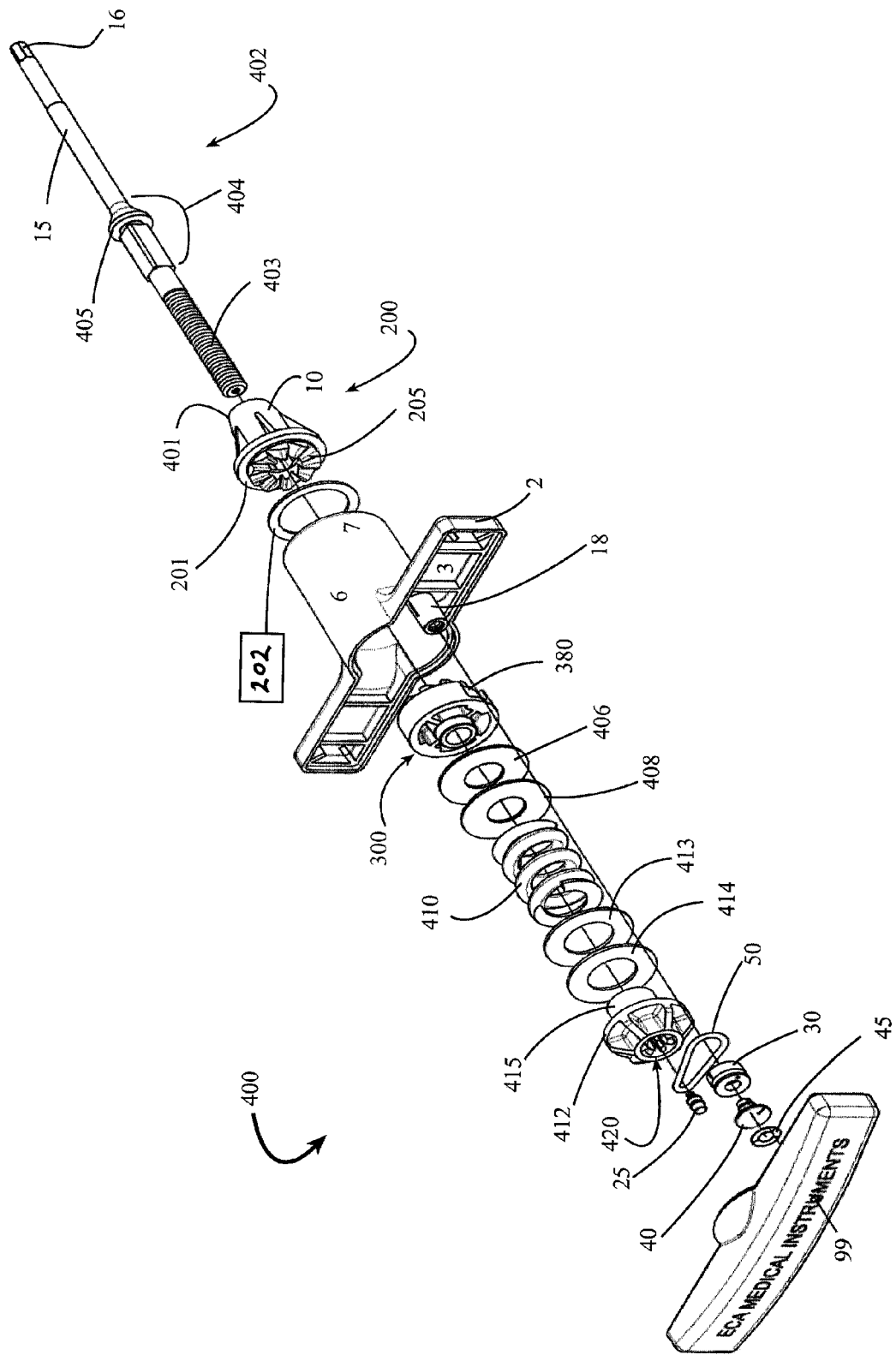
FIG. 5 shows an assembly view of an exemplary implementation of a torque limiting device with belt counter.

Referring generally to FIG. 4 and specifically to FIG. 5, there is an exploded view of a torque-limiting driver 400. The T-shaped handle forms a cavity 3 with a lower cup 2 and upper cover 4. The cup 2 extends into the generally hollow cylindrical body 6 with a cylindrical distal end 7 opposite the T-shaped handle on the cylindrical body 6 and a circumferential rim 9. At the distal end 7, there is nose 10. The nose contains a lower shank 200 and has a circular annular flange 201 to engage said circumferential rim 9 and annularly tapering body along its length. An optional washer, preferably Teflon, a PTFE material, or material with high lubricity, is interposed between said annular flange and the circumferential rim. At one end, the nose 10 tapers to an axial bore 401 at the end of the nose cone 10 molded to engage a pass through member 402. The pass through member 402 has a threaded proximal end 403 and interface 404, and a shaft 15 attached or formed as part thereof at the distal end. The interface also provides a nose catch 405 which restricts axial movement of the pass through member 402 beyond a preset limit. A tool or tool engaging tip 16 is formed at the distal end of the shaft 15. The interface is non-circular in cross section and is formed to mate with the axial bore 401 herein, such that rotating said shaft rotates said lower shank 200. At an opposite end, the lower shank 200 has a plurality of teeth 205 arranged in a crown gear formation. Inside the cylindrical body 6, a clutch assembly is disposed. The clutch assembly includes an upper shank 300 for forcibly engaging the lower shank 200. The upper shank 300 also includes at least one recess 380 on the side of the outer shank. The upper shank 300 has a bottom face that has teeth 382 arranged in a crown gear formation and an annular flange or circumferential rim 383 extending radially outwardly. The recess 380 is provided as a cylindrical cut, relief or recess into the side of the outer shank, and may be provided as a square or rectangular cut, or the cut may have a slanted side or sides relative to the axis of the upper shank 300.

In assembly, the shaft 15 is received into the axial bore 203 of the lower shank 200. A PTFE washer 202 may be provided between the circumferential rim 9 of the lower shank 200 and the circular annular flange 201.

The opposite side of the circular annular flange 201 receives the circumferential rim 383 of the upper shank 300 allowing the teeth 205 of the lower shank 200 to engage the teeth 382 of the upper shank 300 when a torque is applied. Integrally formed within the cylindrical body 6, is a protrusion that mates with the recess 380 of the upper shank 300. The protrusion 385 extends inward in a radial fashion and has a length along the axis of the cylindrical body 6 for relative moveable engagement within the recess 380. This engagement provides a locking mechanism of the pass through member 402, relative to the T-shaped handle via the upper shank when pressure is applied across the lower shank 200 and the upper shank. The recess 380 is provided circumferentially wider than the protrusion 385 for allowing the cylindrical body 6 and the T-shaped handle to rotate in reverse a predetermined distance from a locked position without subsequent reverse rotation of the work-piece-engaging tip 16. Thus, the at least one recess 380 and at least one protrusion 385 lock the T-shaped in one direction providing the necessary torque to drive a fastener and allow for a predetermined amount of reverse rotation before unscrewing a fastener.

In use, force is applied across the lower shank 200 and the upper shank 300 via a spring 410 within the cylindrical body 6. Inside the cylindrical body 6, a series of bearing washers 406 and 408 are provided between the upper shank 300 and the spring 410. The washer transfers pressure from the spring 410 over the top face of the upper shank 300. At an end of the spring 410 opposite the upper shank 300, is a plastic nut with integral shoulder 412. Those of ordinary skill in the art will recognize that a locking nut and washer or shoulder washer in lieu of a plastic nut is within the scope of this disclosure. A pair of nut-bearing washers 413 and 414 is interposed around the neck 415 of the plastic nut 412. When the plastic nut 412 is affixed to the threaded proximal end 403, the arrangement and interposed washers hold the spring 410 in a compressed state. The threaded proximal end 403 engages within an axial bore 420 of the plastic nut 412. Thus, imparting pressure between the respective teeth 382 of the lower shank 200 and the upper shank 300. The spring 410 and the threaded proximal end 403, the nose catch 405 and plastic nut 412 provide the proper tensioning and biasing for the clutch assembly and, generally is adjustable to provide proper tension and calibration. Mounted in the axial bore 420 of the plastic nut 412 is drive shaft 25.

Figure 6:
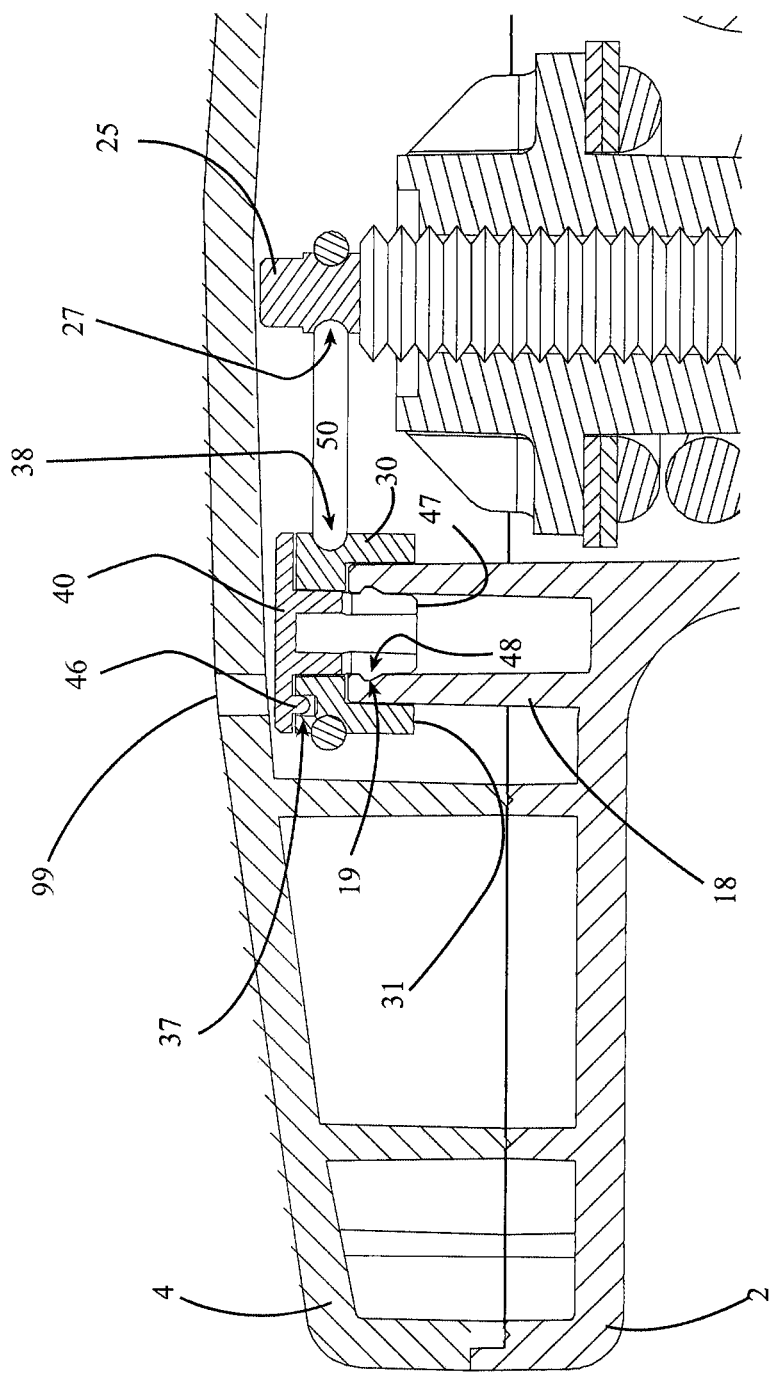
FIG. 6 shows a cutaway view of a belt counter mechanism of some aspects of exemplary implementations of the disclosure.

Referring now to FIGS. 1-5 generally and specifically to FIG. 6, there is shown an indicator wheel 30 supported rotatably on the support post 18 in the cavity 3. The indicator wheel 30 is generally cylindrical with an open bottom 31 and a central guide 32 fluidly connecting the wheel top 34 with the open bottom 31. The indicator wheel further comprises an indicator button guide 37, and a belt wheel guide 38. The indicator button guide is a catch for a latch on the indicator button 40 whereby on the back of the indicator button top 42 is an alignment latch 46 to aligned the indicator button in a single orientation. The indicator button 40 top is attached to a leg 47. The leg is of a size and shape to pass through the central guide 32 and mate with the indicator post 18. The leg provides an extended latch 48 which snap fits into an annular catch 19 within said indicator post 18. Belt 50 is around the drive shaft 25, preferably in an annular drive belt guide 27, whereby rotation of the tip 16 corresponds to a movement of the drive shaft 25, which in turn moves the belt which rotates the indicator button 40 when the torque limiting device is used.

An indicator system or method is disclosed, whereby the belt mediated movement of the indicator wheel and associated indicator button and/or label combination is utilized to provide a visual cue which corresponds to a number of uses or cycles of a device. A device will have a life and an end of life and the indication system and method disclosed herein can visually indicate when the predetermined end of life has been achieved. Or, when the device continues to have useable life. In some instances, a limited use disposable device may be rated for a limited number of uses within a nominal torque range and said indicator system may provide a reference corresponding to number of use, over use, under use or end of life. By selecting the diameter of at least one of the drive belt guide 27 and the indicator button guide 37, the indicator wheel 30 and the drive shaft the amount of movement of the indicator label 45 affixed to the wheel top 34 per use cycle can be selected. Accordingly, a device with very few use cycles can have a indication system that provides a warning of end of life of the device for less use cycles than a device which is designated for a greater number of use cycles.

While the method and apparatus have been described in terms of what are presently considered to be the most practical and preferred implementations, it is to be understood that the disclosure need not be limited to the disclosed implementations. It is intended to cover various modifications and similar arrangements included within the spirit and scope of the claims, the scope of which should be accorded the broadest interpretation so as to encompass all such modifications and similar structures. The present disclosure includes any and all implementations of the following claims.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects of the disclosure both independently and as an overall system and in both method and apparatus modes.

Further, each of the various elements of the disclosure and claims may also be achieved in a variety of manners. This disclosure should be understood to encompass each such variation, be it a variation of an implementation of any apparatus implementation, a method or process implementation, or even merely a variation of any element of these.

Particularly, it should be understood that as the disclosure relates to elements of the disclosure, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this disclosure is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Finally, all referenced listed in the Information Disclosure Statement or other information statement filed with the application are hereby appended and hereby incorporated by reference; however, as to each of the above, to the extent that such information or statements incorporated by reference might be considered inconsistent with the patenting of this/these disclosure(s), such statements are expressly not to be considered as made by the applicant(s).

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular implementation, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative implementations.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

The invention claimed is:

1. A disposable torque limiting device use indicator comprising:
    a torque limiting driver having a body;
    a tool engaging tip on a shaft at a first end of said body;
    a drive shaft rotatable via the movement of said shaft at a second end of said body;
    an indicator wheel mounted to said body viewable at the second end of the body; and,
    a belt interposed between said drive shaft and said indicator wheel whereby movement of the drive shaft is translated into rotation of said indicator wheel.

2. The device of claim 1 wherein said indicator wheel is within said body and viewed through a sight formed in said body.

3. The device of claim 2 further comprising at least a zone with a visual characteristic on said indicator wheel viewable when aligned with said sight.

4. The device of claim 1 further comprising;
a support post; and,
an indicator button affixed through the top of said indicator wheel to said support post.

5. The device of claim 4 wherein said indicator button is within said body and viewed through a sight formed in said body.

6. The device of claim 4 further comprising at least a zone with a visual characteristic on said indicator button.

7. The device of claim 5, further comprising at least two zones with different visual characteristic on said indicator button viewable when aligned with said sight.

8. The device of claim 2 wherein the diameter of at least one of the drive belt guide and the indicator button guide are selected to control the movement of the indicator wheel to delay indication of end of the device's life until a predetermined number of use cycles are completed.

9. A disposable torque limiting device use indicator comprising:
a torque limiting driver having a body with a distal end and a proximal end;
a tool engaging tip on a shaft at a distal end of said driver;
a drive shaft rotatable via the movement of said shaft at said proximal end;
an indicator wheel mounted on a support post at the proximal end of the body with a top;
a belt interposed between said drive shaft and said indicator wheel whereby movement of the drive shaft is translated into rotation of said indicator wheel;
a mounting means whereby said indicator is rotatable about said support post;
at least one visual indicator on said indicator wheel; and,
a sight limited to a partial view of the indicator wheel whereby said at least one visual indicator is viewable when it is aligned with said sight.

10. The device of claim 9 wherein the diameter of at least one of the drive shaft and the indicator wheel are selected to control the movement of the indicator wheel to delay indication of end of the device's life until a predetermined number of use cycles are completed.

11. The device of claim 9 wherein the mounting means is a button affixed through the top of said indicator wheel to said support post.

12. The device of claim 11 wherein the at least one visual indicator is relocated to said button.

13. A method of end of life indication for a disposable torque limiting device, the method comprising:
placing a rotatable indicator wheel which has visual cue information on it within a body of a disposable torque limiting driver;
placing a shaft affixed to a tool inside said body; and,
controlling the movement of the indicator wheel with a belt between the shaft and indicator wheel whereby the wheel movement corresponds to the movement of the shaft.

14. A method of end of life indication for a disposable torque limiting device, the method comprising:
placing a rotatable indicator wheel which has visual cue information on it within a body of a disposable torque limiting driver;
placing a shaft affixed to a tool inside said body; and,
selecting the amount of the movement of the indicator wheel with a belt between the shaft and indicator wheel whereby the wheel movement corresponds to the movement of the shaft.

15. The method of claim 14, further comprising selecting the diameter of the indicator wheel to vary the amount of movement of the indicator wheel per shaft movement.

16. The method of claim 14, wherein the visual cue is one of an alpha numeric, color, pattern, mark, or line indicator.

17. The method of claim 14, wherein the indicator wheel is divided into zones.

* * * * *